US012779081B2

(12) United States Patent
Mount

(10) Patent No.: US 12,779,081 B2
(45) **Date of Patent: *Nov. 3, 2026**

(54) DEVICE FOR REDUCING AIRBORNE CONTAMINANTS

(71) Applicant: Randy A. Mount, Dayton, OH (US)

(72) Inventor: Randy A. Mount, Dayton, OH (US)

( * ) Notice: Subject to any disclaimer, the term of this patent is extended or adjusted under 35 U.S.C. 154(b) by 1020 days.

This patent is subject to a terminal disclaimer.

(21) Appl. No.: 17/972,792

(22) Filed: Oct. 25, 2022

(65) Prior Publication Data

US 2023/0127012 A1 Apr. 27, 2023

Related U.S. Application Data

(60) Provisional application No. 63/271,357, filed on Oct. 25, 2021.

(51) Int. Cl.
*A61L 9/20* (2006.01)

(52) U.S. Cl.
CPC .................................... *A61L 9/205* (2013.01)

(58) Field of Classification Search
CPC ........ A61L 9/205; A61L 9/20; A61L 2209/14; A61L 2209/134; F24F 8/80; F24F 13/24; F24F 8/22; F24F 2013/205; F24F 2110/65; F24F 8/158; F24F 13/06; F24F 13/081; F24F 2110/64; F24F 8/108; F24F 2013/245; F24F 2013/242; F24F 13/20; C02F 2305/10; C02F 2201/326; C02F 1/325; C02F 2201/3228; G02B 5/0891; B01J 2219/1928; B01J 19/0053; B01J 19/123; B01J 2219/0892; B01J 2219/024; B01D 46/0028
See application file for complete search history.

(56) References Cited

U.S. PATENT DOCUMENTS

| | | | | |
|---|---|---|---|---|
| 8,658,101 | B1 * | 2/2014 | Burnett | A61L 9/205 422/24 |
| 9,623,374 | B2 | 4/2017 | Eide | |
| 9,867,897 | B2 | 1/2018 | Eide | |
| 10,391,194 | B2 | 8/2019 | Eide | |
| 10,434,209 | B2 | 10/2019 | Eide | |
| 2022/0120458 | A1 * | 4/2022 | Lee | F24F 8/80 |

* cited by examiner

*Primary Examiner* — Xiuyu Tai
(74) *Attorney, Agent, or Firm* — Thomas E. Lees, LLC

(57) ABSTRACT

To improve effectiveness of photocatalytic systems, a non-planar reflective surface is provided within a photocatalytic system with photocatalytic cells. The non-planar surface reflects ultraviolet (UV) rays in more-desirable directions, thereby permitting greater interaction between the UV rays and the photocatalytic cells. The increased interaction improves the performance of the photocatalytic system. For some embodiments, the non-planar reflective surface comprises a first protrusion and a second protrusion. The protrusions provide larger reflective surfaces as well as more-varied directionality of reflection, as compared to a flat surface.

17 Claims, 7 Drawing Sheets

DEVICE FOR REDUCING AIRBORNE CONTAMINANTS

CROSS REFERENCE TO RELATED APPLICATIONS

This application claims the benefit of U.S. provisional patent application Ser. No. 63/271,352, filed 2021 Oct. 25, by Randy A. Mount, having the title "Device for Reducing Airborne Contaminants," which is incorporated herein by reference in its entirety.

FIELD OF THE DISCLOSURE

The present disclosure relates generally to reducing airborne contaminants and, more particularly, to reducing airborne contaminants using ultraviolet (UV) energy.

DESCRIPTION OF RELATED ART

Ultraviolet (UV) light is a form of electromagnetic radiation with wavelength shorter than that of visible light, but with a wavelength longer than X-rays. UV light is known to interact with organic molecules. More particularly, deoxyribonucleic acid (DNA), ribonucleic acid (RNA), and proteins can absorb deep UV light, e.g., in the range of 200 nanometers (nm) to 300 nm, which can lead to rupture of a cell, disruption of DNA replication, and other molecular damage. As such, UV light is sometimes used to disinfect surfaces that might contain bacteria, mold, virus, etc.

SUMMARY

The present disclosure is directed to photocatalytic systems for reducing airborne contaminants using an ultraviolet (UV) emitter and photocatalytic cells.

Some embodiments include a photocatalytic system for reducing airborne contaminants using an ultraviolet (UV) emitter and photocatalytic cells. For such embodiments, the system comprises a side wall with a wall top, a wall bottom, a wall front edge, and a wall back edge. The system further comprises a front slot that is located toward the wall front edge and a back slot that is located toward the wall back edge. The front slot is configured to secure a front photocatalytic cell, while the back slot is configured to secure a back photocatalytic cell. The side wall further comprises a non-planar reflective surface located between the front slot and the back slot. The non-planar reflective surface permits greater interaction between the UV rays from the UV emitter and the photocatalytic cells, thereby improving the performance of the photocatalytic system. For some embodiments, the non-planar reflective surface comprises a first protrusion and a second protrusion. The protrusions provide larger reflective surfaces as well as more-varied directionality of reflection, as compared to a flat surface.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE EMBODIMENTS

Figure 1A:
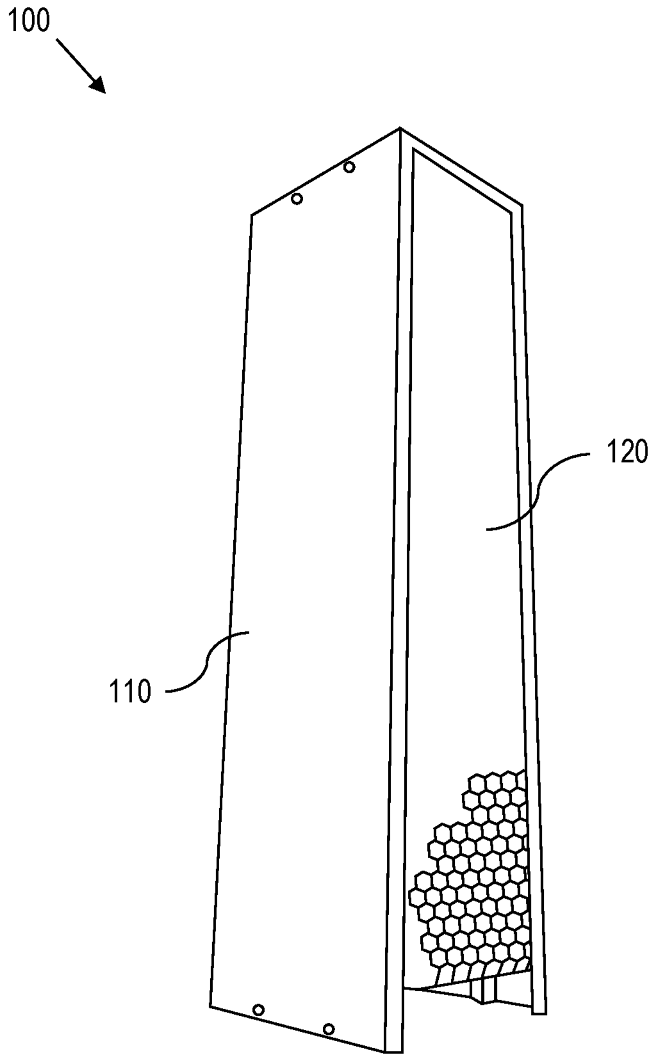
FIG. 1A is a diagram showing a front perspective view of one embodiment of a photocatalytic system for reducing airborne contaminants, which includes a housing and a photocatalytic cell with a honeycomb matrix.

In the presence of ultraviolet (UV) energy, photocatalytic cells produce cluster ions or ionized clouds that reduce airborne contaminants, such as bacteria, mold, or virus. As air passes through the photocatalytic cells, UV energy that strikes the photocatalytic cells results in a catalytic reaction that produces ionized molecules within the airflow. The ionized molecules neutralize some or all of the contaminants that are present in the air.

The effectiveness of photocatalytic systems depends on the concentration of ionized molecules. The concentration of ionized molecules is, in turn, dependent on both: (a) the amount of photocatalytic material on the photocatalytic cells (e.g., titanium dioxide coated on honeycomb structured cells); and, also (b) how much UV strikes the photocatalytic material. In other words, merely having more photocatalytic material (e.g., titanium dioxide) is insufficient if the photocatalytic material is not exposed to the UV energy.

To improve effectiveness of photocatalytic systems, several embodiments are disclosed, which provide for greater UV exposure to the photocatalytic materials. Specifically, some embodiments include a non-planar reflective surface. The non-planar surface permits greater interaction between UV rays and the photocatalytic cells. The increased interaction improves the performance of the photocatalytic system. For some embodiments, the non-planar reflective surface comprises a first protrusion and a second protrusion. The protrusions provide larger reflective surfaces as well as more-varied directionality of reflection, as compared to a flat surface.

Having provided a broad technical solution to a technical problem, reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents.

General Structural Configuration of an Embodiment of a Photocatalytic System

Figure 1B:
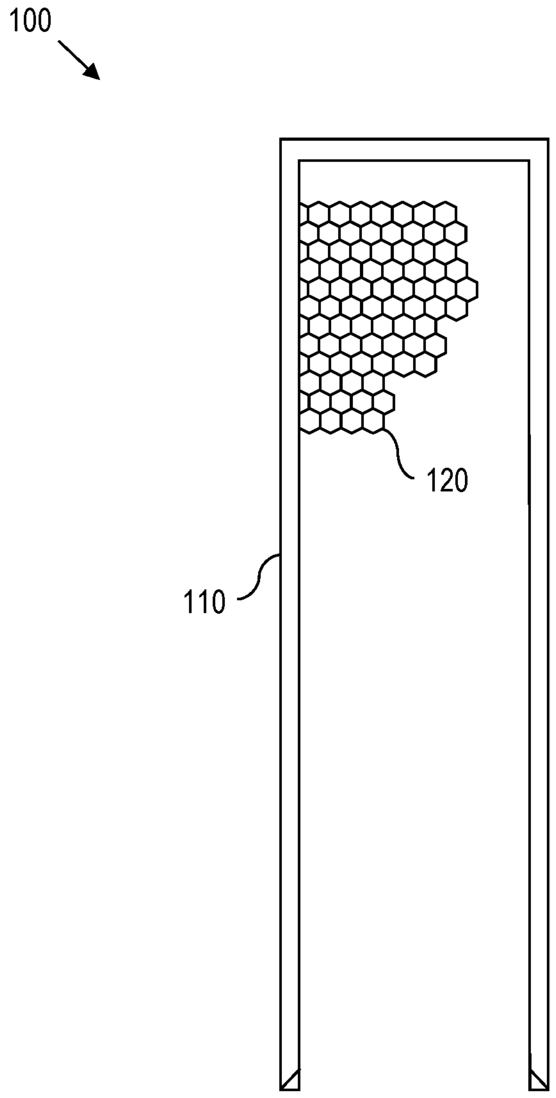
FIG. 1B is a diagram showing a front view of the photocatalytic system of FIG. 1A.
Figure 1C:
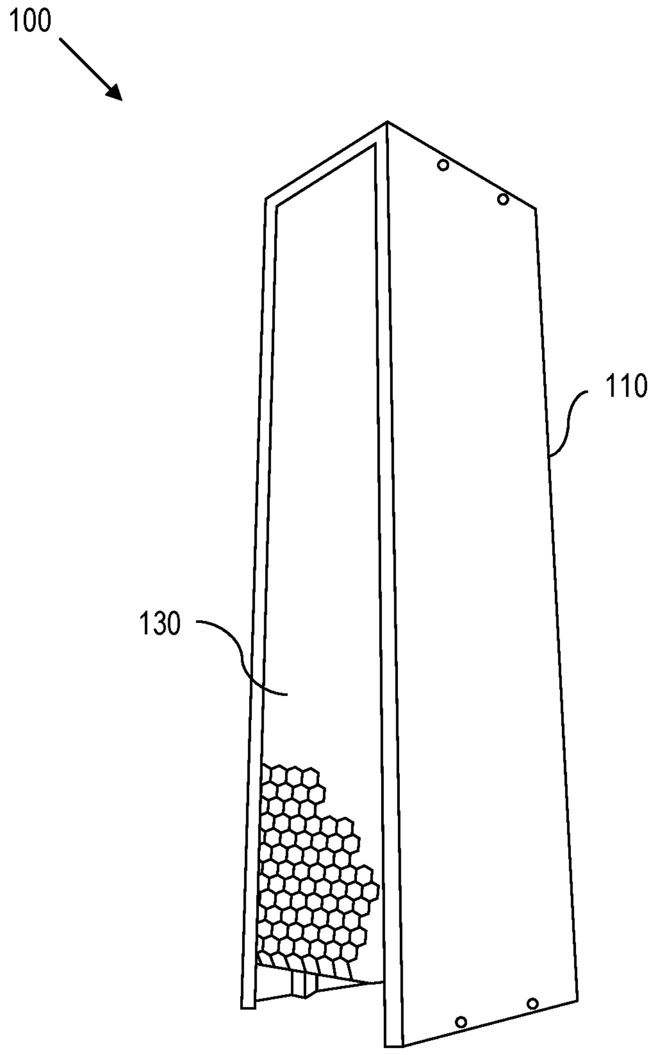
FIG. 1C is a diagram showing a rear perspective view of the photocatalytic system of FIGS. 1A and 1B.
Figure 1D:
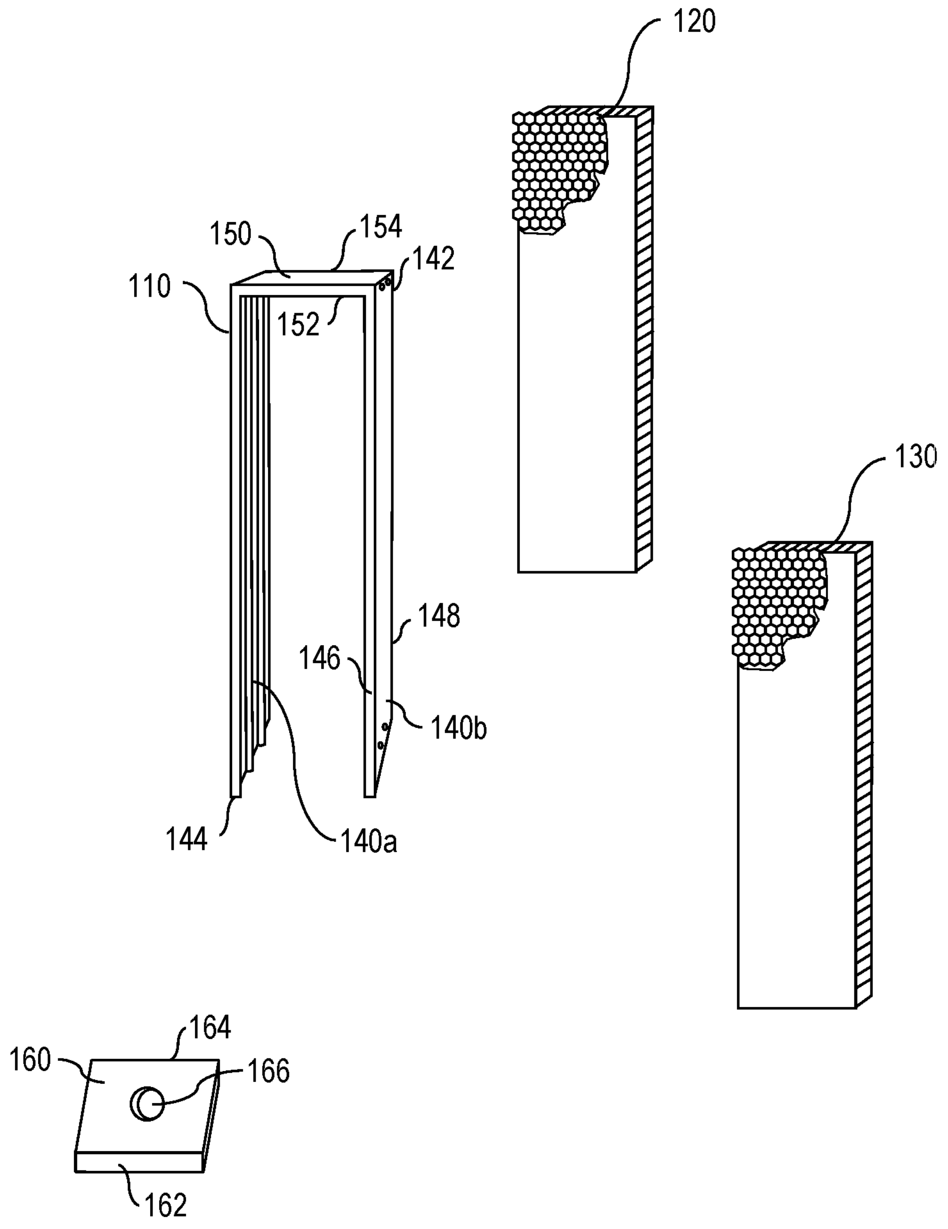
FIG. 1D is a diagram showing an exploded view of the photocatalytic system of FIGS. 1A, 1B, and 1C.

Referring now to the drawings, one embodiment of a photocatalytic system 100 is shown in FIGS. 1A through 1D (collectively designated as FIG. 1). Specifically, FIG. 1A shows a front perspective view, FIG. 1B shows a front view, FIG. 1C shows a rear perspective view, and FIG. 1D shows an exploded view of the embodiment of the photocatalytic system 100. As shown in FIG. 1, the photocatalytic system 100 includes a housing 110, a front photocatalytic cell 120, and a back photocatalytic cell 130. For some embodiments, the photocatalytic cells 120, 130 are substantially rectangular in shape and comprise a honeycomb matrix.

For the embodiment shown, the housing 110 comprises side walls 140*a*, 140*b* (collectively labeled as 140), which are positioned substantially parallel to each other. For some embodiments, the side walls 140 are substantially rectangular in shape, with each side wall 140 having a wall top 142 and a wall bottom 144, with the wall bottom 144 being substantially parallel to the wall top 142.

Furthermore, each side wall 140 has a wall front edge 146, which extends substantially from the wall top 142 to the wall bottom 144, and a wall back edge 148, which is substantially parallel to the wall front edge 146 and also substantially extends from the wall top 142 to the wall bottom 144.

The housing 110 further comprises a housing top 150 that is mechanically coupled to the wall top 142, with the side wall 140 being at substantially right angles to the housing top 150, as shown in FIG. 1C. For some embodiments, the housing top 150 is substantially rectangular in shape and, depending on the particular environment in which the photocatalytic system 100 is used, substantially square in shape. The housing top 150 has a top front edge 152 and a top back edge 154.

The housing 110 further comprises a housing bottom 160 that is positioned substantially parallel to the housing top 150 and mechanically coupled to the wall bottom 144, with the side wall 140 being at substantially right angles to the housing bottom 160. The housing bottom 160 has a bottom front edge 162, a bottom back edge 164, and an opening 166 for receiving the UV emitter. The opening 166 is located between the bottom front edge 162 and the bottom back edge 164. For some embodiments, the housing bottom 160 is substantially rectangular in shape, while for other embodiments the housing bottom 160 is substantially square in shape.

When assembled, the wall front edge 146 extends substantially from the top front edge 152 to the bottom front edge 162. Similarly, the wall back edge 148 extends substantially from the top back edge 154 to the bottom back edge 164. Upon full assembly of the housing top 150, housing bottom 160, side walls 140, the photocatalytic cells 120, 130 and the UV emitter (not shown), the photocatalytic system 100 provides a substantially enclosed environment for the UV emitter.

For some embodiments, the UV emitter is an elongated UV bulb with a proximal end located near the housing bottom 160 and a distal end located near the housing top 150. Because UV bulbs are well known to those having skill in the art, further discussion of the UV bulb itself is omitted herein. In one embodiment, the UV bulb has a proximal end that is located near the housing bottom 160 and secured at its proximal end in or near the opening 166. The UV bulb also has a distal end, which, in some embodiments, is located near the housing top 150. In conventional systems, the distal end of the UV bulb is held by a foam block, which reduces movement of the UV bulb, but detrimentally blocks some of the UV rays from interacting with a portion of the photocatalytic cells.

Unlike foam-block-based systems, a preferred embodiment of the disclosed photocatalytic system 100 comprises a bracket (not shown) that is positioned near the housing top 150, with a substantially circular grommet (not shown) located in the bracket. The grommet is configured to secure the distal end of the UV bulb. In other words, rather than using a foam block (which is used in conventional systems), the disclosed embodiments use a grommet secured to a bracket, which blocks less of the UV rays and, therefore, increases the UV interaction with the photocatalytic cells 120, 130.

With this general configuration for a photocatalytic system 100 described with reference to FIG. 1, attention is turned to FIGS. 2A, 2B, 2C, and 2D (collectively designated as FIG. 2), which shows various features of one embodiment of a side wall 140 in greater detail.

Details of Several Features of an Embodiment of a Side Wall

Figure 2A:
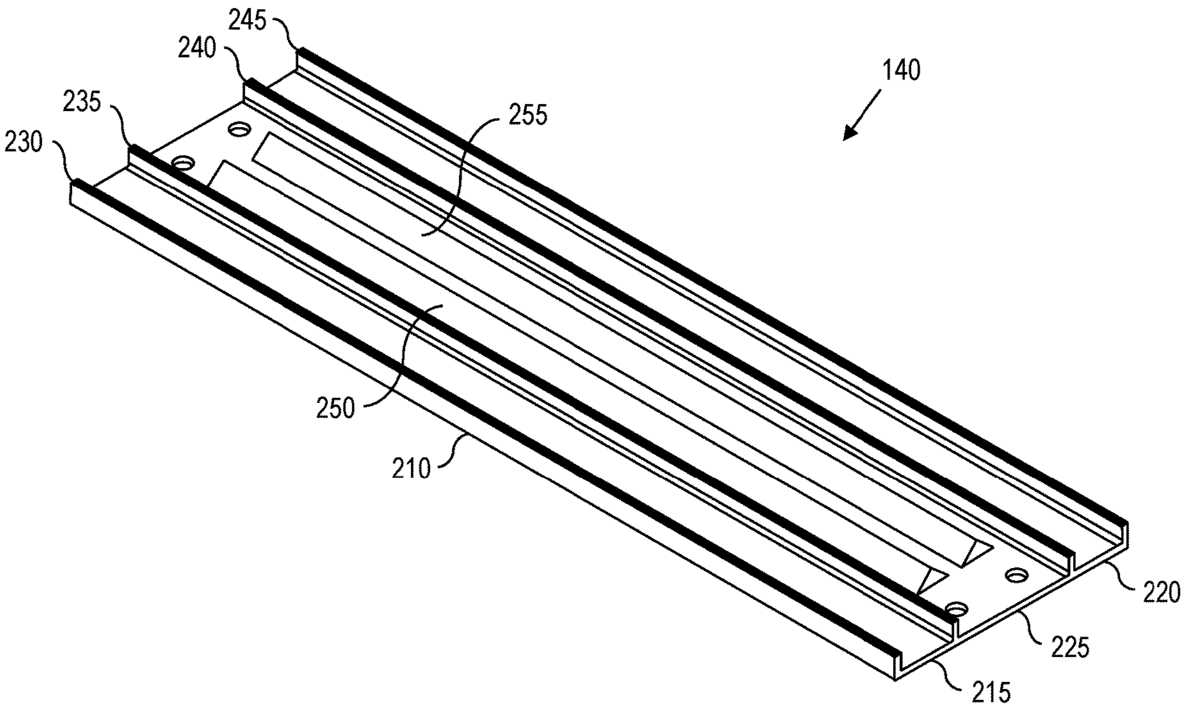
FIG. 2A is a diagram showing a perspective view of one embodiment of a side wall of the photocatalytic system of FIGS. 1A, 1B, 1C, and 1D (collectively designated as FIG. 1).
Figure 2B:
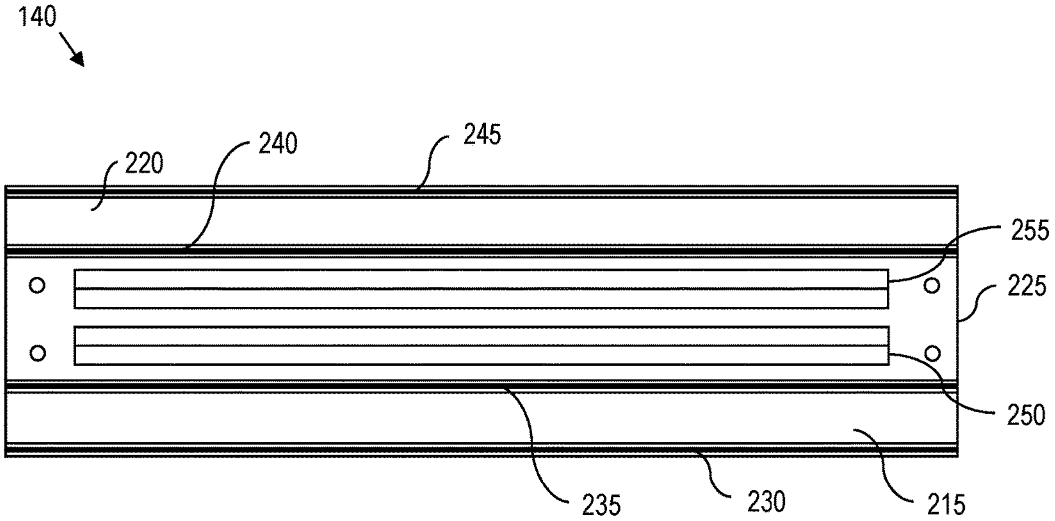
FIG. 2B is a diagram showing a side view of the side wall of FIG. 2A.
Figure 2C:
FIG. 2C is a diagram showing a front view of the side wall of FIGS. 2A and 2B
Figure 2D:
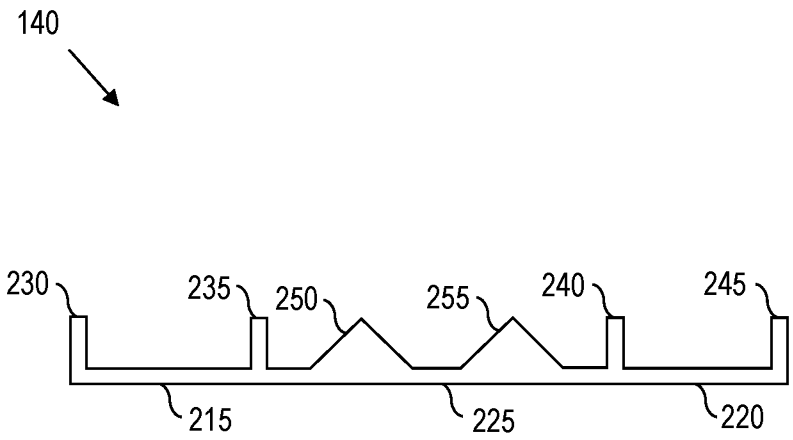
FIG. 2D is a diagram showing a top view of the side wall of FIGS. 2A, 2B, and 2C.

Specifically, FIG. 2A shows a front perspective view of one embodiment of a side wall 140, with FIG. 2B showing a side view, FIG. 2C showing a front view, and FIG. 2D showing a top view of the side wall 140. For consistency, top, front, back, and side are viewed from the same orientation as those designated with reference to FIG. 1.

With this in mind, attention is turned to FIG. 2A, which shows a perspective view of one embodiment of a side wall 140. As shown in FIG. 2A, the side wall 140 comprises a solid structure 210 with a front slot 215, a back slot 220, and a non-planar reflective surface located between the front slot 215 and the back slot 220. For some embodiments, the solid structure 210 is manufactured from aluminum (Al) or steel or some other material that can be polished to provide a surface that reflects light. The front photocatalytic cell 120 is secured in the front slot 215, while the back photocatalytic cell 130 is secured in the back slot 220.

To secure the front photocatalytic cell 120 in place, one embodiment of the front slot 215 comprises two (2) substantially parallel flanges 230, 235, which allow the front photocatalytic cell 120 to slide between the flanges 230, 235. As one can appreciate, the distance between the flanges 230, 235 is approximately the same as the width of the front photocatalytic cell 120 (or slightly larger but within a desired tolerance).

Similarly, to secure the back photocatalytic cell 130 in place, one embodiment of the back slot 225 comprises two (2) substantially parallel flanges 240, 245, which allow the back photocatalytic cell 130 to slide between the flanges 240, 245. Again, the distance between the flanges 240, 245 is approximately the same (within a desired tolerance) as the width of the back photocatalytic cell 130.

Significantly, the non-planar surface 225 is a reflective surface that allows the UV rays to be reflected at different angles (as compared to a flat, planar surface), thereby permitting a greater interaction between the UV rays and the photocatalytic cells 120, 130. This increased interaction correspondingly increases the concentration of ionized molecules, thereby improving the effectiveness of the photocatalytic system 100. For some embodiments, there has been an approximate doubling of the output of ionized molecules with almost negligible ozone production, which is a surprisingly remarkable result than one would normally predict.

Specifically, in one preferred embodiment, the non-planar reflective surface 225 comprises an angled surface, which can be produced by positioning two (2) angled protrusions 250, 255 between the front slot 215 and the back slot 220. As one can appreciate, the number of angled protrusions can be decreased (to one) or increased (to three or more), depending on how many different reflective angles are desired. For other preferred embodiments, the non-planar reflective surface 225 comprises a curved surface (not shown), thereby producing continuously varying angles of reflection. For yet other embodiments, a combination of an angled surface and a curved surface is provided, thereby allowing for a methodically controlled array of reflective angles, which can be custom-tailored to increase UV ray interaction with the photocatalytic cells 120, 130.

Figure 3:
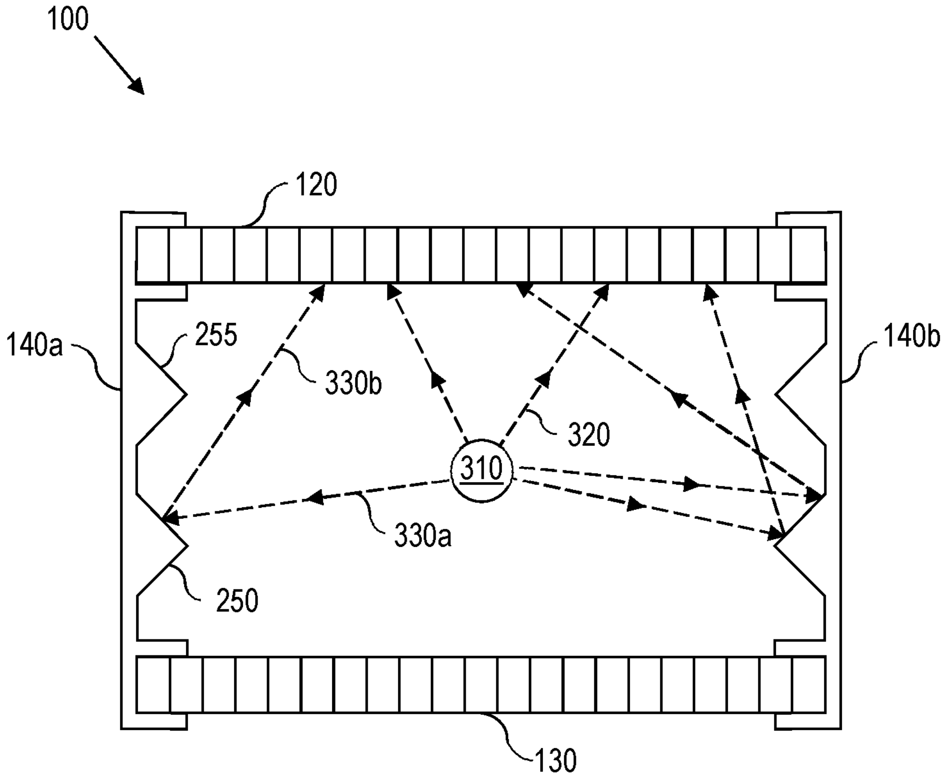
FIG. 3 is a diagram showing a top view of the photocatalytic system with an ultraviolet (UV) bulb in which light rays emanating from the UV bulb and reflected from the side walls are shown.

Turning to FIG. 3, a top view of one embodiment of the photocatalytic system 100 is shown. In the embodiment of FIG. 3, the system 100 comprises an ultraviolet (UV) bulb 310, which emanates light rays 320, 330*a*. Some of the UV rays 320 encounter the photocatalytic cells 120, 130 directly, while other UV rays 330 are reflected from the angled protrusions 250, 255 (or other non-planar reflective surface) before encountering the photocatalytic cells 120, 130. As one can see from FIG. 3, by reflecting the UV rays, the angled protrusions 250, 255 (or other reflective surface) permits greater interaction between the UV rays and the photocatalytic cells 120, 130. Some embodiments exhibit an approximate doubling of the output of ionized molecules with almost negligible ozone production, which is a surprisingly remarkable result than one would normally predict.

Overview of Advantages Using Non-Planar Reflective Surfaces

It should be appreciated that the salient point is that a non-planar reflective surface 225 is provided, which results in a surprising increase in ionization, as compared to conventional systems. Specifically, a catalyst (such as the titanium in the metal oxide) with an appropriate band gap energy allows adsorption of a UV photon to generate electron hole pairs, which initiate a chemical change. For air that is partially or fully saturated with water vapor, the metal oxide surface adsorbs the water vapor to form a partially hydroxylated surface. When exposed to UV energy, the partially hydroxylated surface releases the water vapor in the form of a proton (H) and a hydroxyl (OH (or hydrogen peroxide $H_2O_2$)), which serve as disinfecting agents within the photocatalytic system 100. Thus, as shown in FIGS. 1A through 2D, the non-planar reflective surface 225 improves the effectiveness of the photocatalytic system 100, thereby improving potential health outcomes by disinfecting the air as it passes through the photocatalytic system 100.

Remarkably Better Results Than Expected for Embodiment with Two (2) Angled Protrusions Effectiveness of the photocatalytic system 100 was measured for the embodiment in which the non-planar reflective surface 225 had two (2) angled protrusions 250, 255. Specifically, each angled protrusion 250, 255 had substantially the same surface area on each side of the angle, with the angle being substantially a right angle (namely, approximately ninety degrees (~90°)). In other words, each side of each protrusion 250, 255 was: (a) symmetric about the apex; (b) formed an angle of ~135° with the reflective surface 225; and (c) met at the substantially right-angled apex. This embodiment (with two (2) angled protrusions) produced remarkably better results than expected, as compared to previously published designs by others. To confirm the unexpected results, the effectiveness was measured repeatedly and the average of the measured results were recorded.

Based on the measurements, the two-angled-protrusions embodiment was thirty percent (30%) more effective than a large, single-angled-protrusion side-wall embodiment, such as that shown in U.S. Pat. No. 9,867,897. When tested against other single-angled-protrusion side-walls, the disclosed two-angled-protrusions embodiment was shown to be seventy-three percent (73%) more effective.

As appreciated by those having skill in the art, these are remarkably better results than expected because, typically, improvements in effectiveness of photocatalytic systems are in the single-digit percentages (and not as high as 73%).

Variations and Combinations of Elements

Any process descriptions or blocks in flow charts should be understood as being performed out of order from that shown or discussed, including substantially concurrently or in reverse order, depending on the functionality involved, as would be understood by those reasonably skilled in the art of the present disclosure.

Although exemplary embodiments have been shown and described, it will be clear to those of ordinary skill in the art that a number of changes, modifications, or alterations to the disclosure as described may be made. All such changes, modifications, and alterations should therefore be seen as within the scope of the disclosure.

What is claimed is:

1. A photocatalytic system for reducing airborne contaminants using an ultraviolet (UV) emitter and photocatalytic cells, the system comprising:
- a rectangular housing top comprising:
  - a top front edge; and
  - a top back edge;
- a rectangular housing bottom positioned parallel to the housing top, the housing bottom comprising:
  - a bottom front edge;
  - a bottom back edge; and
  - an opening located between the bottom front edge and the bottom back edge, the opening for receiving the UV emitter; and
- rectangular side walls positioned parallel to each other, each side wall comprising:
  - a wall top mechanically coupled to the housing top at a right angle to the housing top;
  - a wall bottom parallel to the wall top, the wall bottom mechanically coupled to the housing bottom at a right angle to the housing bottom;
  - a wall front edge extending from the top front edge to the bottom front edge;
  - a wall back edge parallel to the wall front edge, the wall back edge extending from the top back edge to the bottom back edge;
  - a front slot located toward the wall front edge, the front slot for securing a front photocatalytic cell;
  - a back slot located toward the wall back edge, the back slot for securing a back photocatalytic cell;
  - a first angled protrusion located between the front slot and the back slot; and
  - a second angled protrusion located between the front slot and the back slot.

2. A photocatalytic system for reducing airborne contaminants using an ultraviolet (UV) emitter and photocatalytic cells, the system comprising:
- a side wall comprising:
  - a wall top;

a wall bottom;

a wall front edge;

a wall back edge;

a front slot located toward the wall front edge, the front slot for securing a front photocatalytic cell;

a back slot located toward the wall back edge, the back slot for securing a back photocatalytic cell;

a first angled protrusion located between the front slot and the back slot; and a second angled protrusion located between the front slot and the back slot.

3. The system of claim 2, wherein the side wall is rectangular.

4. The system of claim 2, further comprising:

the front photocatalytic cell comprising a first honeycomb matrix; and the back photocatalytic cell comprising a second honeycomb matrix.

5. The system of claim 2, wherein:

the front photocatalytic cell comprises a rectangular shape; and the back photocatalytic cell comprises the rectangular shape.

6. The system of claim 2, wherein:

the first angled protrusion comprises a first right-angled apex; and the second angled protrusion comprises a second right-angled apex.

7. The system of claim 6, wherein:

the first angled protrusion is symmetric about the first right-angled apex; and the second angled protrusion is symmetric about the second right-angled apex.

8. The system of claim 2, wherein the first angled protrusion and the second angled protrusion are the same in size.

9. The system of claim 2, further comprising a space between the first angled protrusion and the second angled protrusion.

10. The system of claim 2, further comprising:

a housing top mechanically coupled to the wall top at a right angle, the housing top comprising:

a top front edge aligned with the wall front edge; and a top back edge parallel to the top front edge, the top back edge being aligned with the wall back edge.

11. The system of claim 10, wherein the housing top is rectangular in shape.

12. The system of claim 11, wherein the housing top is square in shape.

13. The system of claim 2, further comprising:

a housing bottom for mechanically coupling to the wall bottom at substantially a right angle, the housing bottom comprising:

a bottom front edge aligned with the wall front edge;

a bottom back edge substantially parallel to the bottom front edge, the bottom back edge being aligned with the wall back edge; and an opening located between the bottom front edge and the bottom back edge, the opening for receiving the UV emitter.

14. The system of claim 13, wherein the housing bottom is rectangular in shape.

15. The system of claim 14, wherein the housing bottom is square in shape.

16. The system of claim 2, wherein the side wall is a first side wall, the system further comprising:

a second side wall positioned parallel to the first side wall, the second side wall being mechanically coupled to the housing top at a right angle to the housing top, the second side wall further being mechanically coupled to the housing bottom at a right angle to the housing bottom.

17. The system of claim 16, wherein the second side wall is rectangular in shape.

* * * * *